United States Patent [19]

Ward et al.

[11] Patent Number: 5,017,572
[45] Date of Patent: May 21, 1991

[54] DERIVATIVES OF 1-[3-(4-HYDROXYPHENYL) 1-HYDROXY 1-PROPYL] BENZENE SUBSTITUTED IN POSITION 2 BY AN AMINOALKYLENEOXY CHAIN, THE METHOD OF PREPARING SAME AND THE APPLICATION THEREOF TO THERAPEUTICS

[75] Inventors: Mona Ward, Courbevoie; Pierre-André Ph.Settembre, Houilles; Alain Renaud, Rueil Malmaison; Michel Langlois, Buc, all of France

[73] Assignee: Delalande S.A., Courbevoie, France

[21] Appl. No.: 339,815

[22] Filed: Apr. 18, 1989

[30] Foreign Application Priority Data

Apr. 22, 1988 [FR] France .................... 88 05382

[51] Int. Cl.$^5$ ............... C07D 223/04; C07D 211/22; C07D 207/08; A61K 31/435
[52] U.S. Cl. .................... 514/218; 514/315; 514/428; 540/609; 546/240; 548/575
[58] Field of Search ............ 540/609; 546/240; 548/575; 514/218, 315, 428

[56] References Cited

U.S. PATENT DOCUMENTS 4,732,896  3/1988  Bourgery et al. ............ 514/212

*Primary Examiner*—Robert Gerstl
*Attorney, Agent, or Firm*—Flynn, Thiel, Boutell & Tanis

[57] ABSTRACT

The present invention relates to compounds of formula:

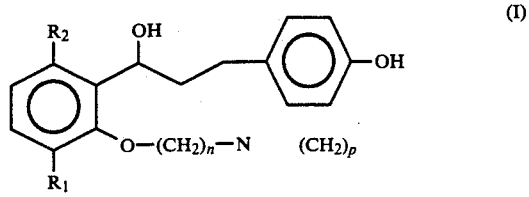

in which:
$R_1$ and $R_2$ are such that:
either $R_1$ represents a methoxy group in which case $R_2$ is a group chosen from the following: hydroxyl; $C_1$-$C_4$ alkyl; $C_2$-$C_8$ alkyloxy; $C_5$-$C_7$ cycloalkyloxy; benzyloxy;
or $R_2$ represents a methoxy group in which case $R_1$ is a group chosen from the following: hydroxyl; $C_2$-$C_8$ alkyloxy; $C_2$-$C_8$ alkyloxy substituted by a methoxy group; $C_1$-$C_4$ trifluoroalkyloxy; $C_3$-$C_4$ alkenyloxy; $C_5$-$C_7$ cycloalkyloxy; benzyloxy; $C_1$-$C_4$ alkyhlthio;
n=2 or 3; and
p=4, 5 or 6, as well as their addition salts with mineral or organic acids, said compounds and salts being useful as drugs.

9 Claims, No Drawings

DERIVATIVES OF 1-[3-(4-HYDROXYPHENYL) 1-HYDROXY 1-PROPYL] BENZENE SUBSTITUTED IN POSITION 2 BY AN AMINOALKYLENEOXY CHAIN, THE METHOD OF PREPARING SAME AND THE APPLICATION THEREOF TO THERAPEUTICS

The present invention relates to new derivatives of 1-[3-(4-hydroxyphenyl) 1-hydroxy 1-propyl]benzene substituted in position 2 by an aminoalkyleneoxy chain, the method of preparing same and the application thereof to therapeutics. More precisely, the derivatives of the invention correspond to the formula:

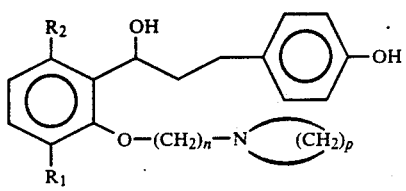

(I)

in which:

$R_1$ and $R_2$ are such that:

either $R_1$ represents a methoxy group in which case $R_2$ is a group chosen from the following: hydroxyl; $C_1$-$C_4$ alkyl $C_2$-$C_8$ alkyloxy $C_5$-$C_7$ cycloalkyloxy benzyloxy;

or $R_2$ represents a methoxy group in which case $R_1$ is a group chosen from the following: hydroxyl; $C_2$-$C_8$ alkyloxy; $C_2$-$C_8$ alkyloxy substituted by a methoxy group; $C_1$-$C_4$ trifluoroalkyloxy $C_3$-$C_4$ alkenyloxy $C_5$-$C_7$ cycloalkyloxy; benzyloxy; $C_1$-$C_4$ alkylthio;

n = 2 or 3; and p = 4, 5 or 6.

The invention also relates to the acid addition salts of these derivatives, these salts being formed with mineral acids such as hydrochloric, sulphuric or phosphoric acid or with organic acids such as fumaric, maeleic, succinic, oxalic, citric or tartaric acid.

In the foregoing and in what follows the expression "$C_1$-$C_4$ alkyl" includes in particular the methyl, ethyl, n-propyl and n-butyl groups; the expression "$C_2$-$C_8$ alkyloxy" includes particularly, ethoxy, n-propyloxy, n-butyloxy, n-pentyloxy, n-hexyloxy, n-heptyloxy and n-octyloxy groups; the expression "$C_5$-$C_7$ cycloalkyloxy" includes cyclopentyloxy, cyclohexyloxy and cycloheptyloxy groups; the expression "$C_3$-$C_4$ alkenyloxy" includes in particular $OCH_2$-$CH$=$CH_2$, $OCH_2$-$CH$=$CH$-$CH_3$ and $OCH_2$-$CH_2$-$CH$=$CH_2$- groups; and the expression "$C_1$-$C_4$ alkylthio" includes particularly methoxythio, ethylthio, n-propylthio and n-butylthio groups.

The present invention further relates to methods of synthesizing the derivatives of formula (I), these methods being in accordance with the reaction diagrams hereafter.

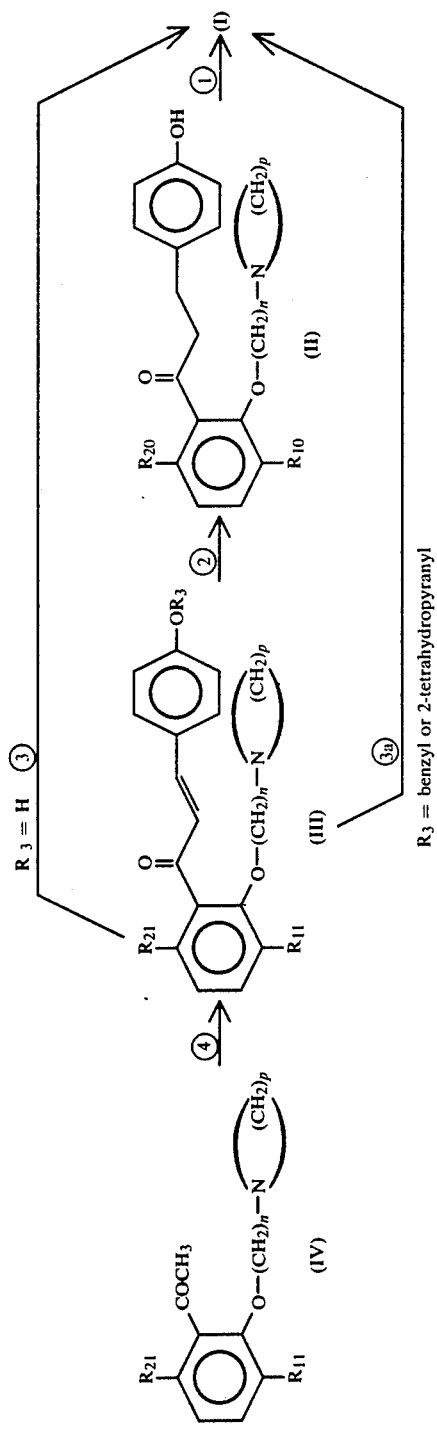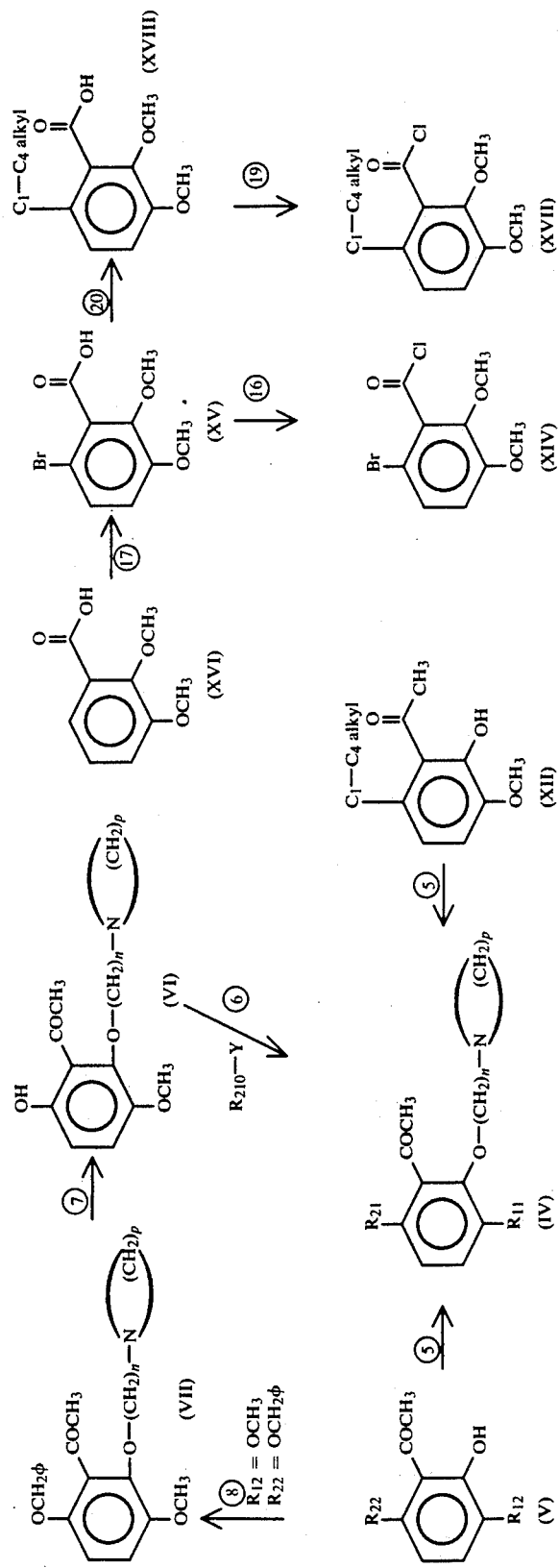

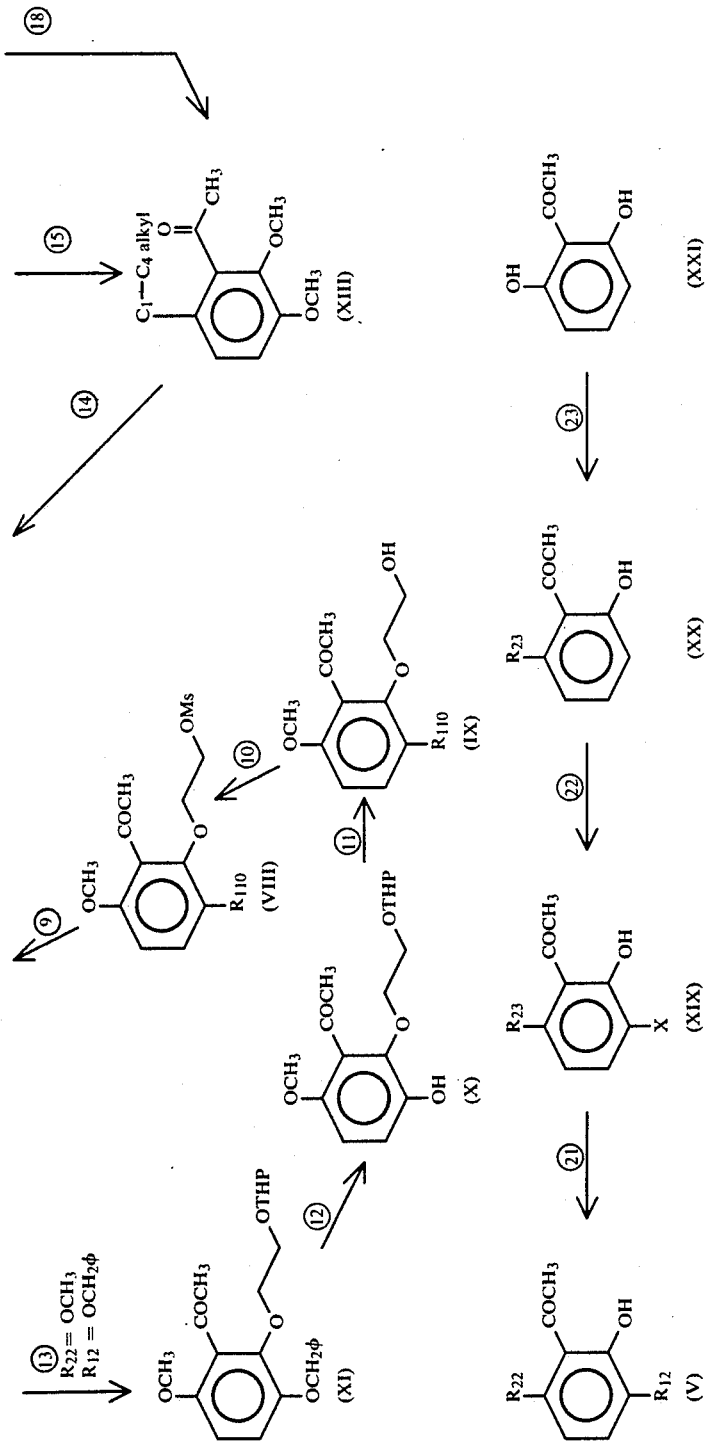

In the above reaction diagrams, the parameters appearing in formulae (1) to (XX) have the following meanings:

n = 2 or 3,
p = 4, 5 or 6,
$R_3$ = H, 2-tetrahydropyranyl or benzyl,
$R_{10}$ and $R_{20}$ have respectively the same meaning as $R_1$ and $R_2$ in the formula (I) with the exception of the benzyloxy group,
$R_{11}$ and $R_{21}$ have respectively the same meaning as $R_1$ and $R_2$ in the formula (I) with the exception of the hydroxyl group,
$R_{210}$ = $C_2$-$C_8$ alkyl or $C_5$-$C_7$ cycloalkyl,
Y = halogene, $OSO_2CH_3$ or $OSO_3C_2H_5$,
$R_{110}$ = $C_2$-$C_8$ alkyloxy or $C_3$-$C_4$ trifluoroalkyloxy,
Ms = mesyl,
THP : 2 TM tetrahydropyranyl,
$R_{12}$ and $R_{22}$ are such that either $R_{12}$ = $OCH_3$ in which case $R_{22}$ = benzyloxy, or $R_{22}$ = $OCH_3$ in which case $R_{12}$ = $C_2$-$C_8$ alkyloxy, $C_2$-$C_8$ alkyloxy substituted by a methoxy group, $C_3$ or $C_4$ alkenyloxy, $C_5$-$C_7$ cycloalkyloxy, benzyloxy or $C_1$-$C_4$ alkylthio,
$R_{23}$ = $OCH_3$ or benzyloxy,
X = Br or I.

Furthermore, the indices ①to ㉓ appearing in these reaction diagrams have the of

①Reduction by sodium borohydride, particularly in an alcohol preferably ethanol medium, in the presence of a base, e.g. NaOH, ②Hydrogenation, particularly in ethanol, in the presence of acid palladium charcoal, ③Reduction by sodium borohydride in ethanol in the presence of pyridine and NaOH, ③a Reduction by sodium borohydride in ethanol followed either by acid hydrolysis when $R_3$ = 2-tetrahydropyranyl, or hydrogenolysis in the presence of palladium on charcoal in ethanol when $R_3$ = benzyl, ④Condensation of the benzaldehyde of formula:

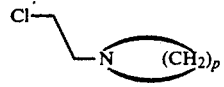

on the compounds (IV) in an alkaline medium in ethanol; when $R_3$ = H, 5 equivalents of 50% NaOH are preferably used whereas when $R_3$ benzyl or 2-tetrahydropyranyl, 2.5 equivalents of 40% NaOH are sufficient, ⑤Condensation of the compound of formula:

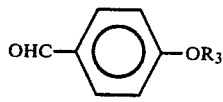

preferably in the form of hydrochloride, on the compounds (V) for which $R_{22}$ = methoxy and $R_{12}$ = $C_2$-$C_8$ alkyloxy, $C_2$-$C_8$ alkyloxysubstituted by methoxy, $C_3$ or $C_4$ alkenyloxy, $C_5$-$C_7$ cycloalkyloxy, benzyloxy or $C_1$-$C_4$ alkylthio, preferably in an aprotic organic solvent such as acetonitrile and in the presence of alkaline metal carbonates such as potassium carbonate, ⑥O-alkylation preferably in an organic solvent such as acetonitrile and in the presence of a base such as potassium carbonate, ⑦Debenzylation by action of hydrogen in the presence of acid palladium on charcoal in an ethanol medium, ⑧Condensation of the compound of formula:

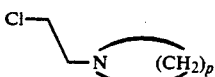

preferably in the form of hydrochloride, on compounds (V) for which $R_{12}$ $OCH_3$ and $R_{22}$ benzyloxy, under the operating conditions as in step 5, ⑨Condensation with the amine of formula:

used in excess and at reflux,

⑩Action of mesyl chloride in an organic solvent in the presence of triethylamine when cold, ⑪Condensation on the compounds (X) of trifluoro ($C_1$-$C_4$) alkyl triflate in acetone in the presence of $K_2co_3$ or of a $C_2$-$C_8$ alkyl halide in DMF in the presence of $K_2CO_3$, followed by acid hydrolysis, ⑫Action of hydrogen in the presence of palladium on charcoal in ethanol, ⑬Action of the compound of formula:

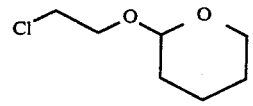

which ($R_{12}$, $R_{22}$) = =$O\Psi H_2\phi$, $OCH_3$),

⑭Demethylation by aluminium chloride, preferably in dichloromethane,

⑮Condensation with 2 equivalents of $CH_3MnI$ in ethyl ether,

⑯Action of thionyl chloride in toluene,

⑰Action of bromine, in the presence of aqueous NaOH, followed by acidification by $H_2SO_4$ at reflux, ⑱Condensation with one equivalent of $CH_3MnI$ in ethyl ether, ⑲Action of thionyl chloride in toluene, ⑳Alkylation by a $C_1$-$C_4$ alkyl halide in the presence of 2 equivalents of n-butyllithium, ㉑Condensation with compounds of formula:

$R_{120}$—O - Na or $R_{121}$—S—Na where $R_{120}$ = $C_2$-$C_8$ alkyl substituted by methoxy ; $C_3$ or $C_4$ alkenyl ; $C_5$-$C_7$ cycloalkyl ; or benzyl, and
$R_{121}$ = $C_1$-$C_4$ alkyl,
in the presence of CuI (when $R_{120}ONa$ is used) or $Cu_2O$ (when $R_{121}SNa$ is used), ㉒Action of bromine in $CHCl_3$ or iodine chloride in acetic acid, ㉓O-alkylation by action of benzyl chloride or bromide methyl sulphate. in acetone in the presence of $K_2CO_3$.

The compounds (I) for which $R_1$ = OH may further be prepared by hydrogenolysis with palladium on charcoal, in an ethanol medium, of the corresponding compounds (1) for which $R_1$ = 0-$CH_2\phi$.

The salts of the derivatives of formula (I) are obtained conventionally, for example, by the action of a mineral or organic acid, in solution with an appropriate solvent, on said derivatives themselves, in solution with an appropriate solvent.

The following preparations are given by way of non limitative examples for illustrating the invention.

EXAMPLE 1

2-Hydroxy 6-methoxy acetophenone [(XX) ; $R_{23}$ =$OCH_3$]

Code number : 9

A mixture of 25 mmoles of 2,6-dihydroxy acetophenone, 26 mmoles of methyl sulphate, 75 mmoles of $K_2CO_3$ and 60 ml of acetone are heated to reflux for 12 hours. Then the reaction medium is cooled, the mineral matter is separated by filtration and rinsed with dichloromethane. After evaporation of the organic phase and flash chromatography, the expected product is obtained in a practically quantitave way (mp =55° C).

With the same operating conditions, but using benzyl bromide in place of 2,6-dihydroxy acetophenone, 2-hydroxy 6-methoxy acetophenone [(XX), $R_{23}$ =$OCH_2\phi$; code number 42] is obtained with a yield of 60 % (mp =109° C).

EXAMPLE 2

3-Bromo 2-hydroxy 6-methoxy acetophenone [(XIX); X TM Br, $R_{23}$ =$OCH_3$]

Code number : 10

By action of the bromine on the compound of code number 9 prepared in the preceding example, in methylene chloride, using the technique described by C.L. COON, W.G. BLUTCHER, M.E. HILL, J. Org. Chem. 38, 4Z43 (1973), the expected compound is obtained with a yield of 76 % (mp =101° C).

In the same way, but starting with the compound of code number 4Z, 3-bromo 2-hydroxy 6-benzyloxy acetophenone is obtained [(XIX), $R_{23}$=$OCH_2\phi$, X=Br; code number 43] with a yield of 84 % (mp =124° C.; $IR_{KBr}$; peak CO at 1620 cm$^{-1}$).

EXAMPLE 3

2-Hydroxy 3-iodo 6-methoxy acetophenone
[(XIX) ; $R_{23}$ =$OCH_3$, X =I]

Code number : 13

409g (2.45 moles) of acetophenone of code number 9 prepared in example 1 is solubilized in 3 liters of crystallizable acetic acid. At the same time, 420g (2.60 moles) of iodine chloride are solubilized in 400 ml of acetic acid. At 17° C, the iodine chloride solution is added in 15 minutes to the solution of the acetophenone. After 10 minutes agitation, the reaction is finished. Then the mixture obtained is poured on 10 liters of cold water and the whole is agitated for 30 minutes, then filtered, drained, rinsed with 2 litres of water, drained, dried for 1 hour 30 minutes in a ventilated oven at 50° C and the product is recrystallied in ethanol to isolate 634g (yield =88 %) of the expected compound.

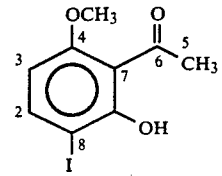

melting point =115° C.,
$IR_{KBr}$: peak CO at 1615 cm$^{-1}$,
NMR$^{13}$C (CDCl$_3$, TMS) : shift in ppm
$C_2$ =144.7 ; $C_3$ =103.8 ; $C_4$ =55.9 1.
$C_5$ =33.2 ; $C_6$ =204.7 ; $C_7$ =115.5
$C_8$ =75.7

EXAMPLE 4

2-Hydroxy 3-allyloxy 6-methoxy acetophenone (V), $R_{12}$ =allyloxy, $R_{22}$ =$OCH_3$]

Code number 15.

With nitrogen scavenging, 0.1 ml of sodium hydride dispersed at 80% in oil is covered by 30 ml of DMF. A solution of 0.12 mole of allylic alcohol in 20 ml of DMF, is added drop by drop, without exceeding 30° C. At the end of adding, agitation is carried out for 1 hour at 20° C. Then 0.025 mole of the compound of code number 13 prepared in example 3 and 0.0026 mole of CuI is added, then agitation is carried out for 1 hour at about 80° C. At the end of the reaction, the reaction medium is poured on 150 ml of water, the pH is adjusted to 3 with dilute hydrochloric acid, it is extracted with ethyl ether, the organic phase is dried on $Na_2SO_4$, it is dry evaporated and purified by flash chromatography (eluent : heptane (85) ethyl acetate (15). Thus the expected compound is isolated with a yield of 45 %.

Using a similar method, but from appropriate reagents and using 0.035 mole of Cu20 in place of 0.0025 mole of CuI when alkylthioalcohol is used in the place of allylic alcohol, the other compounds (V) are obtained, shown in the following table I, as well as 2-hydroxy 3-methoxy 6benzyloxy acetophenone [(V), $R_{12}$ =$OCH_3$, $R_{22}$ =$OCH_2\phi$] of code number 44 (mp =103° C ; IR (KBr) : band CO at 1625 cm$^{-1}$)

TABLE I

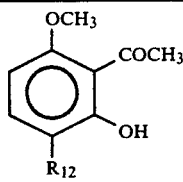

(V)

Compounds (V) Common spectral data:
IR (KBr): band CO at 1620 cm$^{-1}$
NMR $^1$H (CDCl$_3$), TMS):
  6.9 and 6.3 ppm, 2d (2H), Ar—H
  about 13 ppm, 1s (1H), O—H
    3.8 ppm, 1s (3H), O—CH$_3$
    2.6 ppm, 1s (3H), COCH$_3$
  Melting

| Code | point |

TABLE I-continued

| Number | $R_{12}$ | (°C.) | NMR $^1$H (CDCl$_3$, TMS) of the protons of $R_{12}$ |
|---|---|---|---|
| 7b | CH$_3$CH$_2$O— | 70 | 4 ppm,q(2H),OC$\underline{H}_2$CH$_3$;3 ppm,t(3H), OCH$_2$C$\underline{H}_3$ |
| 14 | CH$_3$(CH$_2$)$_2$O— | 90 | 3.9 ppm,m(2H),OC$\underline{H}_2$R;1.7 ppm,m(2H), OCH$_2$C$\underline{H}_2$CH$_3$;1 ppm,m(3H),OCH$_2$CH$_2$C$\underline{H}_3$ |
| 15 | CH$_2$=CHCH$_2$O— | oil | from 5 to 6 ppm,m(3H),C$\underline{H}_2$=C$\underline{H}$;4.5 ppm,d(2H), CH$_2$=CH—C$\underline{H}_2$O |
| 16 | φCH$_2$O | " | 7.3 ppm,m(5H),Ar$\underline{H}$;5 ppm,s(2H),OC$\underline{H}_2$Ar |
| 17 | CH$_3$O(CH$_2$)$_2$O— | 63 | 4 ppm,t(2H),ArOC$\underline{H}_2$CH$_2$R;3.7 ppm,m(5H), ArOCH$_3$ + —C$\underline{H}_2$OCH$_3$;3.4 ppm,s(3H),ROC$\underline{H}_3$ |
| 18 | cC$_6$H$_{11}$O— | oil | 3.9 ppm,s + t(4H),OC$\underline{H}_3$ + ArOC$\underline{H}$RR'; 1.5 ppm,m(10H),C$\underline{H}_2$cyclohexyl |
| 21 | CH$_3$S— | 83 | 7.3 ppm,d(1H),(J:8HZ)Ar$\underline{H}$;2.3 ppm,s(3H), C$\underline{H}_3$S |
| 22 | CH$_3$CH$_2$S— | 57 | 7.4 ppm,d(1H),(J:8Hz)Ar$\underline{H}$;2.8 ppm,q(2H), CH$_3$C$\underline{H}_2$S;1.2 ppm,d(3H),C$\underline{H}_3$CH$_2$S |

EXAMPLE 5

2-(2-Piperidino ethoxy) 3-methoxy 6-benzlyloxy acetophenone [(VII) ; n =2, p =5]

Code number : 45

A mixture of 0.15 mole of the compound of code number 44 prepared in accordance with example 4, 0.15 mole of N-(Z-chloroethyl) -piperidine hydrochloride, 0.46 mole of K$_2$CO$_3$ and 750 ml of acetonitrile is brought to reflux for 2 hours. Then, it is cooled, filtered, dry evaporated, the residue is taken up with 300 ml of ethyl ether, the organic phase is washed with 50 ml of water, dried on Na$_2$SO$_4$ and evaporated. After purification using the usual techniques, the expected compound is obtained with a yield of 87 % (IR$_{KBr}$ : CO band at 1710 cm$^{-1}$)

EXAMPLE 6

2-(2-Piperidino ethoxy) 3-methoxy 6=hydroxy acetophenone [(VI) ; n =2, p =5]

Code number : 46

To a solution of 30 mmoles of the compound of code number 45 prepared in example 5 in 100 ml of ethanol are added 2g of 10% palladium on charcoal containing 50 % humidity and hydrochoric ethanol traces. Agitation is carried out for 2 hours at 20° C in a hydrogen atmosphere. Then the medium is filtered, the catalyst is rinsed with ethanol and the medium is dry evaporated so as to obtain the expected compound with a yield of 82 %, in the form of a pure oil (IR$_{KBr}$:CO band at 1640 cm$^{-1}$).

EXAMPLE 7

O-alkylation in position 6 of the acetophenone of code number 46 prepared in example 6 for obtaining the compounds of formula (IV) where $R_{11}$ =OCH$_3$.

A mixture of 20 mmoles of the acetophenone 46, 22 mmoles of a compound of formula $R_{210}$-Y defined in the following table II, 60 mmoles of K2C03 and 70 ml of acetonitrile is heated to reflux. Once the reaction is finished (4–120 hours), the mixture is dry evaporated, taken up with water, extracted with ethyl ether, the hydrochloride is extracted from the organic phase by 1N HCl, the aqueous phase is washed with ethyl ether, the O-alkylated acetophenone is salted out from the aqueous phase with NH$_4$OH, extracted with ethyl ether, dried on MgSO$_4$, dry evaporated and the oil obtained is filtered on silica (eluent : dichloromethane then ethyl acetate), this oil corresponding to the expected compounds (IV). A number of these compounds are shown in the following table II.

TABLE II

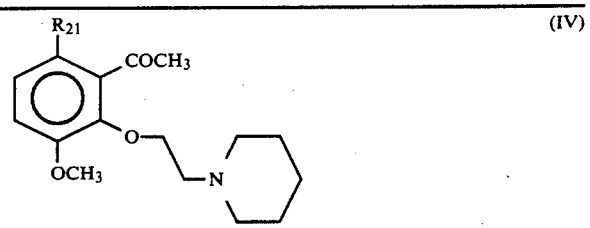

(IV)

Compounds (IV) Common spectral data:
IR (KBr): band CO at 1710 cm$^{-1}$
NMR $^1$H (CDCl$_3$, TMS):
6.6 ppm, q (2H), Ar—$\underline{H}$
4.1 ppm, t (2H), O—C$\underline{H}_2$—C$\underline{H}_2$—N
3.7 ppm, s (3H), O—C$\underline{H}_3$ 2.5 ppm, m + s (9H), CO—C$\underline{H}_3$, C$\underline{H}_2$—N(CH$_2$/CH$_2$)

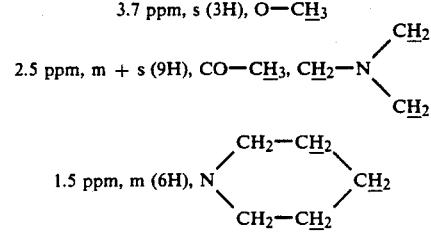

| Code number | $R_{21}$ | $R_{210}$—Y | NMR $^1$H (CDCl$_3$), TMS) of the protons of $R_{21}$ |

TABLE II-continued

| | | | |
|---|---|---|---|
| 47 | CH$_3$(CH$_2$)$_3$O | I | 4 ppm,m(4H) dont RCH$_2$O;1.5 ppm,m (10H) including CH$_3$(CH$_2$)$_3$O;1 ppm,m (3H),CH$_3$ |
| 48 | CH$_3$(CH$_2$)$_2$O | Br | 3.9 ppm,m(4H) dont RCH$_2$O;1.5 ppm, m(8H) including CH$_3$CH$_2$CH$_2$O;1 ppm,m (3H),CH$_3$ |
| 49 | (CH$_3$)$_2$CHO | Br | 4.3 ppm,m(1H),(CH$_3$)$_2$CHO;1.3 ppm, d(6H),(CH$_3$)$_2$CHO |
| 50 | CH$_3$(CH$_2$)$_7$O | OMs | 3.8 ppm,m(4H) dont OCH$_2$R;1.4 ppm,m, (21H) including OCH$_2$(CH$_2$)$_6$CH$_3$ |
| 51 | cC$_6$H$_{11}$O | Oms | 4.1 ppm,m(3H) including CH(CH$_2$)$_5$;1.5 ppm, m(16H) including CH(CH$_2$)$_5$ |
| 52 | CH$_3$CH$_2$O | OSO$_3$Et | 4 ppm,m(4H) dont CH$_3$CH$_2$O;1.3 ppm, m(9H) including CH$_3$CH$_2$O |

EXAMPLE 8

Preparation of the acetophenones of formula (IV where R$_{21}$=OCH$_3$.

the operating mode used is that described for example 5, but using the compounds (V) as starting products where R$_{22}$=OCH$_3$.

A number of the coumpounds thus synthesized (which are all in the form of oil) are shown in the following table III.

TABLE III

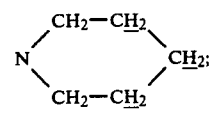
(IV)

| Code number | R$_{11}$ | Starting compounds | Remarks - Special treatments |
|---|---|---|---|
| 100 | CH$_3$CH$_2$O | 7b | — |
| 101 | CH$_3$(CH$_2$)$_2$O | 14 | — |
| 102 | CH$_2$=CHCH$_2$O | 15 | Purification by recristallization of the oxalate in acetone |
| 103 | φCH$_2$O | 16 | Hydrochloride mp = 180° C. |
| 104 | CH$_3$O(CH$_2$)$_2$O | 17 | — |
| 105 | cC$_6$H$_{11}$O | 18 | — |
| 106 | CH$_3$S | 21 | Chromatography CH$_2$Cl$_2$(95) MeOH (4,5) NH$_4$OH (0,5) |
| 107 | CH$_3$CH$_2$S | 22 | Chromatography CH$_2$Cl$_2$ (95) MeOH (4,5) NH$_4$OH (0,5) |

It should also be noted that for these compounds : in $^1$H NMR, the peaks corresponding to the aminated ether

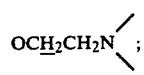

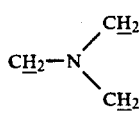

in IR, the CO band appears at 1680-1700 cm$^{-1}$.

EXAMPLE 9

2,3-Dimethoxy 6-bromo benzoic acid (XV)

Code number : 7Z 91 g (0.5 mole) of 2,3-dimethoxy benzoic acid (XVI) are solubilized in 1.2 l of 1.6 N NaOH, cooled to 0° C ; 38.4 ml (0.75 mole) of bromine are added and agitation is carried out for 30 minutes at +5° C.

Then the mixture is acidifed, using HCl, extracted with ethyl ether and the organic phase washed with sodium thiosulphate, dried and evaporated. The residue is taken up in 200 ml of ethanol, 3 drops of sulphuric acid are added and it is left at reflux one night. Then it is dry evaporated, the residue is taken up with 300 ml of ethyl ether, the aqueous phase is extracted with 300 ml of 2N NaOH, the aqueous phase is washed with ethyl ether before being dried on Na$_2$SO$_4$ in the presence of animal black. Then it is filtered, evaporated and dried. Thus, !07g of the pure expected compound are isolated, which is crystallisable in a petroleum ether (50) - toluene (50) mixture.

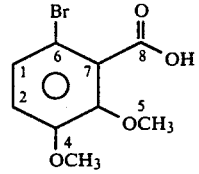

mp=87° C.

IR$_{KBr}$ : CO band at 1710 cm$^{-1}$ mass spectrum : molecular peak at 261

13$_C$ NMR (CDCl$_3$)

C$_1$ = 128.1
C$_2$ = 115
C$_4$ = 56.Z
C$_5$ = 61.9
C$_6$ TM 108.7
C$_7$ = 118.3
C$_8$ = 170.6

EXAMPLE 10

2,3-Dimethoxy 6-bromo benzoic acid chloride (XIV)
Code number : 73

6.8 mmoles of the acid of code number 72 prepared in the preceding example are agitated with 34 mmoles of thionyl chloride in 5 ml of toluene for 48 hours. Then, the mixture is dry evaporated and the excess thionyl chloride is eliminated by azeotropic distillation of the toluene. The resultant expected compound is used as it is in the method of example 11.

EXAMPLE 11

2,3-Dimethoxy 6-methyl acetophenone (XIII)
Code number : 75

0.250 mole of $MnI_2$ is dispersed in 800 ml of ethyl ether freshly distilled on $LiAlH_4$. At 0° C. 0.24 mole of methyllithium (1.6N solution in ethyl ether) is added in 15 minutes, then agitation is carried out for half an hour at 0° C, then for 2 hours at ambient temperature. Then the reaction medium is cooled to 0° C and 0.12 mole of the compound of code number 73 prepared in example 10 and diluted with 50 ml of ethyl ether is added. After reaction for half an hour at 0° C, then for 2 hours 30 mins at 25° C, 1Z0 ml of 2N ammonia are added, agitation is carried out for 15 minutes, the reaction mixture is neutralized with hydrochloric acid, extracted with ethyl ether, the organic phase is washed with a thiosulphate solution, then it is dried and dry evaporated. The expected is obtained with a yield of 88 %.

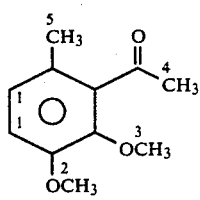

IR(KBr) : CO band at 1700 cm$^{-1}$
$^{13}C$ NMR : $C_1 = 113.3 - 125.9$
(CDCl$_3$)
$C_2 = 56$
$C_3 = 61.5$
$C_4 = 32.3$
$C_5 = 18.2$
$C_6 = 205$

EXAMPLE 12

2, 3-Dimethoxy 6-ethyl benzoic acid (XVIII)
Code number : 94

13g (50 mmoles) of the acid (XV) of code number 72 are dissolved in 160 ml of THF at $-100°$ C. and 67 ml (107 mmoles) of a 1.6N n-butyllithium solution are slowly added. It is left under agitation for 15 minutes and 37.6 ml (500 mmoles) of ethyl iodide are added. It is left for 1 hour at $-90°$ C., then for 1 hour at $-60°$ C. and 1 hour at 20° C. The reaction medium is poured on 2N HCl. The aqueous phase is extracted with ethyl ether. The organic phase is dried and concentrated. The residue is taken up in ethanol with a few drops of $H_2SO_4$ and heated to reflux overnight and concentrated. The residue is taken up with the NaOH (2N) - ethyl ether mixture. After extraction, the aqueous phase is acidified with HCl and extracted with ethyl ether. After drying of the organic phase followed by its concentration, 8.24g of the expected product is obtained in the form of an oil.

IR$_{KBr}$:CO band 1700 cm$^{-1}$OH band : 3100 cm$^{-1}$

EXAMPLE 13

2,3-Dimethoxy 6-ethyl benzoic acid chloride
Code number : 97

This compound is prepared using an operating mode similar to that of example 10, but from the compound of code number 94.

Yield : 77 %
IR$_{KBr}$ : CO band at 1795 cm$^{-1}$.

EXAMPLE 14

2, 3-Dimethoxy 6-ethyl acetophenone (XIII)
Code number : 98

This compound is prepared using an operating mode similar to that for example 11, but from the compound of code number 97.

IR$_{KBr}$ : CO band at 1705 cm$^{-1}$.

EXAMPLE 15

2-Hydroxy 3-methoxy 6-methyl acetophenone (XII)
Code number : 92

To a solution of 8.32g (43 mmoles) of the compound of code number 75 prepared in example 11, in 100 ml of $CH_2Cl_2$ at 0° C., 5.7g (43 mmoles) of $AlCl_3$ are added, agitation is carried out for 1 hour at 0° C, then 6 hours at reflux. Then the reaction mixture is cooled and it is poured on 50 ml of concentrated hydrochloric acid, extracted with ethyl acetate, the organic phase is washed with water then dried on $Na_2SO_4$ and dry evaporated. After purification by chromatography, 5.93g of a pure yellow oil are obtained which corresponds to the expected compound.

IR$_{KBr}$ : CO band : 1690 cm$^{-1}$OH band : 3400 cm$^{-1}$.

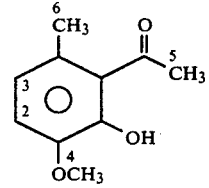

(CDCl$_3$) $C_4 = 56.2$
$C_5 = 32.5$
$C_6 = 21.2$

EXAMPLE 16 2-(2-Piperidino ethoxy) 3-methoxy 6-methyl acetophenone [(IV) ; n = 2, p = 5,
$R_{11} = OCH_3$, $R_{21} = CH_3$]
Code number : 108

This compound is prepared using an operating mode similar to that of example 5, but from the compound of code number 92 prepared in example 15.

The IR and 1H NMR spectra of the compound in question have the characteristics mentioned for example 8.

EXAMPLE 17

2-[2-(2-Tetrahydropyranyloxy) ethoxy]3-benzyloxy 6-methoxy acetophenone (XI)
Code number : 31

5.44 g (20 mmoles) of the compound of code number 16 prepared in accordance with example 4, 4.8 g (29 mmoles) of Z-(Z-chloroethoxy) tetrahydropyrane and 8.3 g (60 mmoles) of $K_2CO_3$ are heated to reflux for 5 days in acetonitrile. Then the mixture is dry evaporated, the residue is taken up with 25 ml of water, extracted with 35 ml of ethyl ether, dried and evaporated after filtration on silica (eluent dichloromethane). 3.95 g of the expected compound are recovered which is in the form of an oil.

$IR_{KBr}$: CO band : 1710 cm$^{-1}$

EXAMPLE 18

2-[2-(2-Tetrahydropyranyloxy) ethoxy 3-hydroxy 6-methoxy acetophenone (X)

Code number : 32

3.95g (10 mmoles) of compound of code number 31 obtained in the preceding example are agitated with 0.8g of 10% Pd on charcoal containing 50 % of water in a hydrogen atmosphere at 20° C. After a night in contact, the catalyst is separated by filtration, rinsed with ethanol and the residue is dry evaporated. Thus, 3.05 g of the expected compound are isolated.

mp = 83° C $IR_{KBr}$: CO band : 1700 cm$^{-1}$ OH band : 3300 cm$^{-1}$.

EXAMPLE 19

2-(2-Hydroxyethoxy) 3-(2,2,2-trifluoroethoxy) 6-methoxy acetophenone [(IX), $R_{11O} = OCH_2CF_3$]

Code number : 33a

The mixture of 5.75 g (18.5 mmoles) of the compound of code number 3Z prepared in the preceding example, 8.6 g (34.4 mmoles) of trifluoroethyl triflate, 7.68 g (55.6 mmoles) of $K_2CO_3$ and 60 ml of acetone are heated to reflux. After 3 hours of contact, the mixture is filtered, dry evaporated, taken up with a 3N hydrochloric ethanol (25 ml) water (25 ml) mixture. After agitation then neutralization with sodium bicarbonate, it is dry evaporated, the evaporation residue is taken up with 50 ml of water, the aqueous phase is extracted with ethyl ether, the extract is dried and dry evaporated. Thus, 4.47 g of the expected compound are obtained in the form of pure oil.

$IR_{KBr}$: CO band : 1700 cm$^{-1}$ OH band : 3430 cm$^{-1}$.

EXAMPLE 20

2-(2-Hydroxyethoxy) 3-isopropyloxy 6-methoxy acetophenone [(IX), $R_{11O} = OCH(CH_3)_2$]

Code number : 33b 5.7g (18.5 mmoles) of the compound of code number 32 obtained in example 18 are dissolved in 60 ml of DMF. 2.23g (56 mmoles) of powdered NaOH are added, the mixture is warmed to 50° C and 3.5 ml (37 mmoles) of isopropyl bromide are added. After Z hours 30 minutes at 50° C., the reaction mixture is poured into 200 ml of water and extracted with twice 200 ml of ethyl ether. The ether phases are agitated for a few minutes with 15 ml of concentrated hydrochloric acid, then washed with water then with a sodium bicarbonate solution, dried and evaporated. Thus, 4.97 g of a pure oil are isolated which correspond to the expected compound.

$IR_{KBr}$: CO band : 1700 cm$^{-1}$ OH band : 3350 cm$^{-1}$

EXAMPLE 21

2-(Z-Mesyloxyethoxy) 3-(Z,2,2-trifluoroethoxy) 6-methoxy acetophenone [(VIII), $R_{11O} = CF_3CH_2O$ ]

Code number : 34a 14 mmoles of the compound of code number 33a are dissolved in 50 ml of dichloromethane. 21 mmoles of triethylamine are added. The mixture is cooled to 0° C. and 15 mmoles of mesyl chloride are added very slowly. At the end of addition, agitation is carried out for 30 minutes at 0° C., then the mixture is washed with water, dried on $Na_2SO_4$ and dry evaporated. Thus, the expected compound is isolated.

$IR_{KBr}$: CO band at 1710cm$^{-1}$

Using the same method, but from the compound of code number 33b, Z-(Z-mesyloxyethoxy) 3-isopropoxy 6-methoxy acetophenone is obtained whose code number is 34b [(VIII), $R_{11O} = OiPr$].

EXAMPLE 22

2-(2-Piperidino ethoxy) 3-(2,2,2-trifluoro ethoxy) 6-methoxy acetophenone [(IV), n =2, p =5, $R_{11} = OCH_2CF_3$, $R_{21} = OCH_3$]

Code number ; 35a 12.9 mmoles of the compound of code number 34a prepared in the preceding example in 500 mmoles of piperadine are brought to boiling point. Then, it is dry evaporated, taken up with ethyl acetate, extracted with 2N HCl, the aqueous phase is washed with ethyl ether, the product of this phase is salted out by the addition of $NH_4OH$, then extracted with ethyl acetate. The organic phase is washed several times with water than dried on $Na_2SO_4$, filtered and evaporated. Thus, the expected compound is obtained in the form of an oil.

$^1H$ NMR (CDCl$_3$, TMS) : 6.7ppm, q(2H). Ar-H ; 4.3 ppm. m(4H), Ar—O—CH$_2$—CF$_3$ and Ar—O—CH$_2$CH$_2$—N ; 7 ppm, s(3H), OCH$_3$ ; 2.5 ppm, m(9H), CO-CH3 and

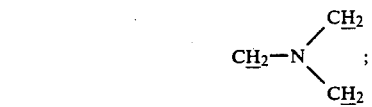

1.5 ppm, m(6H)

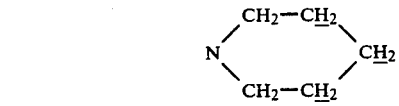

Similarly, but from the compound of code number 34b, 2 -(2-piperadinoethoxy) 3-isopropoxy 6-methoxy acetophenone (IV), n =2, p =5, $R_{11}$=OiPr, $R_{21}$ =OCH$_3$]is obtained whose code number is 35b.

$^1H$ NMR (CDCl$_3$, TMS) : 6.7 ppm, q(2H), Ar-H ; 4.2 ppm, t +m (3H), ArOCH$_2$CH$_2$N +ArOCH(CH$_3$)$_2$ ; 1.4 ppm, d +m (12H), (CH$_2$)$_3$+CH(CH$_3$)$_2$

EXAMPLE 23

1-[2-(2-Piperidino ethoxy) 3 TM allyloxy 6-methoxy phenyl]3-(4-hydroxyphenyl) 2-propen 1-one [(III), n =2, p =5, $R_{11}$ =allyloxy, $R_{21}$ =OCH$_3$, $R_3$ =H]

Code number : 125

7.7g (23 mmoles) of the compound of code number 102 prepared in accordance with example 8 are solubilized in ml of ethanol, 3.1g (Z5 mmoles) of 4-hydroxy benzaldehyde and 4.6g (110 mmoles) of 50% aqueous NaOH are added and then the mixture is agitated at 20° C tor 3 days. Then the alcohol is evaporated, the residue is taken up with water, washed with isopropyl ether, acidifed with hydrochloric acid (the hydrochloride precipitates), the heterogeneous aqueous phase is washed with isopropyl ether, the aqueous phase is treated with 50 ml of 5N NH$_4$OH, extracted with ehhyl acetate, then the organic phase is dried, evaporated and the product obtained is crystallized in 50 ml of ethyl acetate. Thus, 6.03g of the expected compound are isolated. mp = 132° C.

$IR_{KBr}$: CO band : 1650 cm$^{-1}$. OH band : 3400 cm$^{-1}$.

Using the same operating method, but trom appropriate reagents, the compounds of code numbers 120, 122 and 126 shown in the following table IV are obtained.

EXAMPLE 24

1-[-[2-(2-Piperidino ethoxy) 3-methoxy 6-benzyloxy phenyl]3-{4-[(2-tetrahydropyranyl)oxy]phenyl}2-propen 1-one [(III), n = 2, p = 5, Rll = OCH3, $R_{21}$ = OCH$_2\phi$, $R_3$ = 2-tetrahydropyranyl]

Code number : 114

56.6g (148 mmoles) of the compound of code number 45 prepared in example 5 and 30g (148 mmoles) of 4-(2-tetrahydropyranyl) oxy benzaldehyde are dissolved in 600 ml of ethyl alcohol. Then, 37 ml (370 mmoles) of 10N aqueous NaOH are added, agitation is carried out for 5 hours at 25° C., the alcohol is concentrated to 3/4, the reaction mixture is poured in 1 litre of water, extracted with twice 200 ml of CH$_2$Cl$_2$, the organic phase is washed with three times 200 ml of water, dried and evaporated. The expected product is crystallized in ethyl ether and thus 65g of the expected compound are isolated.

mp = 103° C.

$IR_{KBr}$ : CO band at 1650 cm$^1$

Using the same method, but from the appropriate reagents, the compounds of code numbers 110, 114–19, 124 and 127–131 shown in table IV herebelow are obtained.

EXAMPLE 25

Reduction of the compounds (III) for which $R_3$ = H, prepared in the preceding example, for obtaining the corresponding compounds (I)

10 mmoles of compound (III) with R3 = H are dissolved in 150 ml of ethanol. 50 mmoles of pyridine and 25 mmoles of 10N NaOH are added and the mixture is brought to reflux. Then, 50 to 100 mmoles of sodium borohydride are added in 3 hours. At the end of the reaction, the reaction mixture is poured on 700 ml of iced 0.5N HCl, agitation is carried out for 30 minutes at 0° C, then the product is salted out with ammonia, extracted with CH$_2$Cl$_2$, the organic phase is washed with water, dried on Na$_2$SO$_4$, evaporated, purified by flash chromatography [eluent : CH$_2$Cl$_2$(95)—CH3OH (4.5)—NH$_4$OH (0.5)], crystallized in ethyl acetate and recrystallized if required in ethanol. Using this method, the compounds of code numbers 167 and 168 shown in the following table V are obtained, respectively from the compounds of code numbers 125 and 26.

EXAMPLE 26

Reduction of the compounds (III) for which $R_3$ = 2-tetrahydropyranyl, prepared in example 24, for obtaining the corresponding compounds (I).

10 mmoles of compound (III) with $R_3$ = 2-tetrahydropyranyl are heated to reflux in 100 ml of ethanol containing a drop of NaOH. 50 mmoles of sodium borohydride are added in 3 hours, then the medium is cooled, dry evaporated, the residue is taken up with 150 ml of ethyl acetate, poured on 10 ml of HCl at 0° C., the mixture is agitated for 15 minutes, then salted out by ammonia, extracted with three times 120 ml of ethyl acetate, the organic phase is washed with a sodium chloride saturated solution, dried on Na$_2$SO$_4$, dry evaporated and purified by flash chromatography [eluent : CH$_2$Cl$_2$ (97) —CH$_3$OH (2.7) —NH$_4$ OH (0.3)]

Using this method the compounds of code numbers 146, 174 and 175 shown in table V were

TABLE IV

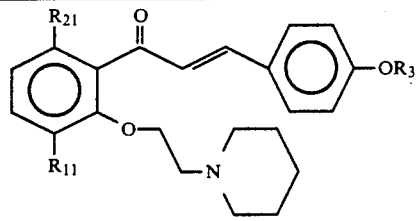

(III)

| Code number | $R_{11}$ | $R_{21}$ | $R_3$ | Code No. of the starting compound | Melting point (°C.) | Purification treatments |
|---|---|---|---|---|---|---|
| 110 | CF$_3$CH$_2$O | CH$_3$O | H | 35a | oil | Filtered on silica |
| 114 | CH$_3$O | BzO | THP | 45 | 103 | Crist. in Et$_2$O |
| 115 | CH$_3$O | CH$_3$(CH$_2$)$_3$O | Bz | 47 | oil | — |
| 116 | CH$_3$O | CH$_3$(CH$_2$)$_2$O | Bz | 48 | " | — |
| 117 | CH$_3$O | (CH$_3$)$_2$CHO | Bz | 49 | " | — |
| 118 | CH$_3$O | CH$_3$(CH$_2$)$_7$O | Bz | 50 | " | — |
| 119 | CH$_3$O | cC$_6$H$_{11}$O | Bz | 51 | " | — |
| 120 | CH$_3$O | CH$_3$CH$_2$O | H | 52 | 124 | Crist. in Et$_2$O |
| 122 | CH$_3$CH$_2$O | CH$_3$O | H | 100 | 153 | Crist. in Et$_2$O |
| 124 | CH$_3$(CH$_2$)$_2$O | CH$_3$O | Bz | 101 | oil | — |
| 125 | CH$_2$=CH—CH$_2$O | CH$_3$O | H | 102 | 132 | Crist. in AcOEt |
| 126 | BzO | CH$_3$O | H | 103 | 137 | Crist. in AcOEt |
| 127 | CH$_3$O(CH$_2$)$_2$O | CH$_3$O | Bz | 104 | oil | Filtered on silica |
| 128 | cC$_6$H$_{11}$O | CH$_3$O | Bz | 105 | " | Filtered on silica |
| 129 | CH$_3$S | CH$_3$O | THP | 106 | 88 | Chromat. then crist./iPr$_2$O |
| 130 | CH$_3$CH$_2$S | CH$_3$O | THP | 107 | oil | Filtered on silica |
| 131 | CH$_3$O | CH$_3$ | Bz | 108 | " | Filtered on silica |
| — | CH$_3$O | C$_2$H$_5$ | Bz | — | " | — |

THP = 2-tetrahydropyranyl
Bz = benzyl obtained respectively from the compounds of code numbers 114, 129 and 130.

EXAMPLE 27

Reduction of the compounds (III) prepared in example 24 for obtaining the corresponding compounds (I).

First step : preparation of the compounds (II)

10 mmoles of the compounds (III) are dissolved in an ethyl alcohol (50) ml - THF (50 ml) mixture, 20 % by weight of 10% Pd on charcoal containing 50 % humidity is added, and agitation is carried out at 20° C in a hydrogen atmosphere. At the end of the reaction, the catalyst is separated by filtration, rinsed with THF, the mixture is dry evaporated and recrystallized in an appropriate solvent.

Thus, the compounds (II) shown in table VI below are obtained.

Second step : reduction of the compounds (II) into the corresponding compounds (I).

10 mmoles of compounds (II) obtained in the preceding step are dissolved in 50 ml of ethanol, 1 ml of 10N NaOH (i.e. 10 mmoles) is added, the mixture is heated to reflux and then from 50 to 100 mmoles of sodium borohydride are added in 3 hours. At the end of the addition, the mixture is maintained at reflux for 2 hours, cooled, dry. evaporated, taken up with ethyl acetate, poured on 25 ml of 2N HCl at 0° C., agitated for 15 minutes at 0° C, neutralized with NH4OH, extracted with twice 100 ml of ethyl acetate, dried, dry evaporated, chromatographed on silica if necessary [eluent : $CH_2Cl_2$ (95) - $CH_3OH$ (4.5)-$NH_4OH$ (0.5)], crystallized and recrystallized if required.

Thus, the compounds (I) are shown in table V other than those of code numbers 146, 167, 168, 174 and 175.

TABLE V (I)

| Code number | $R_1$ | $R_2$ | Melting point (°C.) | Recrystallization solvent |
|---|---|---|---|---|
| 137 | $CF_3CH_2O$ | $CH_3O$ | 117 | $Et_2O$ |
| 146 | $CH_3O$ | BzO | 153 | $CH_3OH$ |
| 148 | $CH_3O$ | OH | 153 | AcOEt |
| 150 | $CH_3O$ | $CH_3(CH_2)_3O$ | 123 | AcOEt |
| 152 | $CH_3O$ | $CH_3(CH_2)_2O$ | 124 | $Et_2O$ |
| 154 | $CH_2O$ | $(CH_3)_2CHO$ | 140 | $iPr_2O$ |
| 156 | $CH_3O$ | $CH_3(CH_2)_7O$ | 113 | $iPr_2O$ |
| 158 | $CH_3O$ | $cC_6H_{11}O$ | 157 | AcOEt |
| 160 | $CH_3O$ | $CH_3CH_2O$ | 148 | AcOEt |
| 164 | $CH_3CH_2O$ | $CH_3O$ | 119 | AcOEt |
| 166 | $CH_3(CH_2)_2O$ | $CH_3O$ | 99 | $iPr_2O$ |
| 167 | $CH_2=CH-CH_2-O$ | $CH_3O$ | 131 | AcOEt |
| 168 | BzO | $CH_3O$ | 148 | EtOH |
| 169 | OH | $CH_3O$ | 134 | AcOEt |
| 171 | $CH_3O(CH_2)_2O$ | $CH_3O$ | 110 | $Et_2O$ |
| 173 | $cC_6H_{11}O$ | $CH_3O$ | 142 | AcOEt |
| 174 | $CH_3S$ | $CH_3O$ | 155 | iPrOH |
| 175 | $CH_3CH_2S$ | $CH_3O$ | 117 | AcOEt |
| 177 | $CH_3O$ | $CH_3$ | 170 | $CH_2Cl_2$ |
| — | $CH_3O$ | $C_2H_5$ | 136 | $Et_2O$ |

TABLE VI

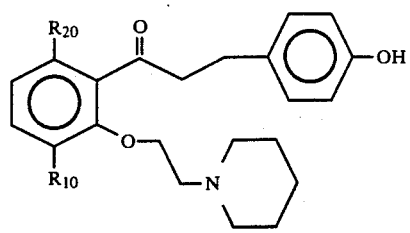

(II)

| Code number | $R_{10}$ | $R_{20}$ | Melting point (°C.) | Recrystallization solvent |
|---|---|---|---|---|
| 136 | $CF_3CH_2O$ | $CH_3O$ | oil | — |
| 147 | $CH_3O$ | OH | 104 | $C_2H_5OH$ |
| 149 | $CH_3O$ | $CH_3(CH_2)_3O$ | 131 | Acetone |
| 151 | $CH_3O$ | $CH_3(CH_2)_2O$ | 142 | " |
| 153 | $CH_3O$ | $(CH_3)_2CHO$ | 157 | " |
| 155 | $CH_3O$ | $CH_3(CH_2)_7O$ | oil | — |
| 157 | $CH_3O$ | $cC_6H_{11}O$ | 107 | Isopropyl ether |
| 159 | $CH_3O$ | $CH_3CH_2O$ | 120 | Isopropyl ether |
| 163 | $CH_3CH_2O$ | $CH_3O$ | 115 | Isopropyl ether |
| 165 | $CH_3(CH_2)_2O$ | $CH_3O$ | oil | — |
| 170 | $CH_3O(CH_2)_2O$ | $CH_3O$ | 100 | Isopropyl ether |
| 172 | $cC_6H_{11}O$ | $CH_3O$ | 154 | Ethyl ether |
| 176 | $CH_3O$ | $CH_3$ | oil | — |
| — | $CH_3O$ | $C_2H_5$ | oil | — |

The compounds (I) and their pharmacologically acceptable salts have been studied on laboratory animals and have shown pharmacological activities and particularly a calcium antagonistic activity.

The calcium antagonistic activity was shown by the test of the contractions of the removed basilar artery of a rabbit in a hyperpotassic medium as described by K. Towart, S. Kazda in Nimodipine Pharmacological Properties edited by P.E. Betz, K. Deck and F. Hoffmeister (1984), publisher : E.K. Schattauer Verlag.

The protocol of this test is the following. The rabbit is anaesthetized with pentobarbital at a dose of 30 mg/kg then sacrificed by exsanguiation and decapitated at the third cervical vertebra. The basilar artery is removed (1 5 cm) between the vertebral arteries and the Willis's polygon. The basilar artery is then cut in a spiral at an angle of 45° . It is fixed by means of a curved needle between an L shaped glass support and a movement sensor (Grass, type FT03). A mechanical tension of 500 mg is applied to the vessel, before letting it reach its equilibrium condition.

For a period of 1 hour, the vessel is rinsed every 20 minutes, until a stable level is obtained.

The tonic contraction following depolarization caused by KCl is dependent on the calcic movements for it is abolished by the suppression of calcium in the survival medium.

The concentrations (in nM) are measured which reduce by 50% the amplitude of the contraction induced by the KCl at 35 mmoles.

The results obtained with some compounds of the invention in the preceding test are shown, by way of example, in the following table VII which further shows the acute toxicity (LD 50) of some of the compounds tested and which is estimated on mice using the method of J.T. LITCHFIELD and F. WILCOXON, J. Pharmacol. Exp. Ther. 1949, 96, 99.

TABLE VII

| Code number | IC$_{50}$ (nM) | LD$_{50}$ Mice (mg/kg/i.v.) |
| --- | --- | --- |
| 169 | >100 | |
| 164 | 24 | 17 |
| 137 | >100 | |
| 166 | 120 | |
| 167 | 53 | |
| 171 | >100 | |
| 173 | >100 | |
| 168 | >100 | |
| 174 | 27 | 22 |
| 175 | 31 | |
| 148 | >100 | |
| 160 | 6 | 11,7 |
| 154 | 13 | |
| 152 | 10 | |
| 158 | >100 | |
| 150 | 100 | 21,5 |
| 156 | >100 | 27,5 |
| 146 | >100 | |
| 177 | 30 | |

Taking into account the foregoing, the compounds (I) and their pharmaceutically acceptable salts find their use in human or animal therapeutics for treating affections related to a disturbance of the intra and extra cellular movements of calcium at the cerebral level and particularly for treating the troubles of the cerebrovascular system, such as cerebral hemorrhages, cerebral infarct and migraine.

Another object of the present invention consists then in the use of the compounds of the invention for preparing medicaments for treating the above mentioned affections and particularly pharmaceutical compositions which comprise at least one of these compounds in association with a physiologically acceptable support or excipient appropriate for said compounds.

These compositions may for example be formulated for oral, parenteral or rectal administration.

For oral administration, said compositions may be in the form of tablets, sugar-coated pills or capsules prepared by the usual techniques using known supports and excipients such as binding agents, fillers, lubricants and disintegration agents; they may also be in the form of solutions, syrups or suspensions.

For parenteral administration, the compositions of the invention may be in the form of injectable solutions, suspensions or emulsions comprising a liquid, oily or aqueous vehicle, parenterally acceptable.

Finally, for rectal administration, the compositions of the invention may be in the form of suppositories comprising the usual bases for suppositories.

The dose at which the active ingredients, namely the compounds of the invention, may be administered to man or any hot blooded animal, depends more particularly on the type of administration, the body weight and the pathological state of the patient and the therapeutical power of the compounds used. Generally, when taken orally, the doses may reach 500 mg of active ingredient per day (divided into one or more doses); parenterally, the doses may reach 100 mg of active ingredient per day (in one or more daily injections) and rectally, the doses may reach 300 mg of active ingredient per day (in one or more suppositories).

What is claimed is:

1. Compounds of formula :

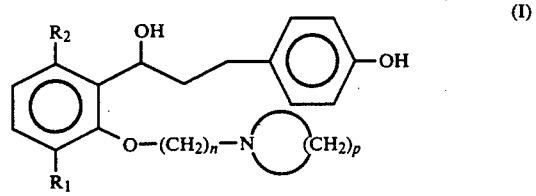

in which :
R$_1$ and R$_2$ are such that :
either R$_1$ represents a methoxy group in which case R$_2$ is a group chosen from the following : hydroxyl; C$_1$-C$_4$ alkyl C$_2$-C$_8$ alkyloxy C$_6$-C$_7$ cycloalkyloxy benzyloxy;
or R$_2$ represents a methoxy group in which case R$_1$ is a group chosen from the following : hydroxyl; C$_2$-C$_8$ lkyloxy ; C$_2$-C$_8$ alkyloxy substituted by a methoxy group; C$_1$-C$_4$ trifluoroalkyloxy C$_3$-C$_4$ alkenyloxy C$_5$-C$_7$
cycloalkyloxy ; benzyloxy ; C$_1$-C$_4$ alkylthio ;
n = 2 or 3 ; and
p = 4, 5 or 6,
as well as their addition salts with mineral or organic acids.

2. Compounds and salts according to claim 1, in which R$_1$ = methoxy and R$_2$ is a group chosen from the following : benzyloxy, hydroxyl, n-butyloxy, n-propyloxy, i-propyloxy, n-octyloxy, cyclohexyloxy, ethoxy, methyl, ethyl.

3. Compounds and salts according to claim 1, for which R$_2$ = methoxy and R$_1$ is a group chosen from the following : 2,2,2-trifluoroethoxy, ethoxy, n-propyloxy, allyloxy, benzyloxy, hydroxyl, 2-methoxy ethoxy, cyclohexyloxy, methylthio, ethylthio.

4. Compounds and salts according to claim 1, in which R$_1$ is methoxy and R$_2$ is ethoxy.

5. Compounds and salts according to claim 1, in which R$_1$ is ethoxy and R$_2$ is methoxy.

6. Compounds and salts according to claim 1, in which r$_1$ is methoxy and R$_2$ is propoxy.

7. Compounds and salts according to claim 1, in which r$_1$ is methoxy and R$_2$ is isopropoxy.

8. A pharmaceutical composition having calcium antagonistic activity comprising a pharmaceutically effective amount of a compound or salt according to claim 1, together with a pharmaceutically acceptable diluent, carrier, vehicle or excipient.

9. A method of treating a patient suffering from a cerebral hemorrhage, cerebral infarct or migraine headache which comprises administering to such patient a pharmaceutically effective amount of the composition as claimed in claim 8.

* * * * *

UNITED STATES PATENT AND TRADEMARK OFFICE
CERTIFICATE OF CORRECTION

PATENT NO. : 5 017 572
DATED : May 21, 1991
INVENTOR(S) : Mona WARD et al It is certified that error appears in the above-identified patent and that said Letters Patent is hereby corrected as shown below:

Column 24, line 20; after "cloalkyloxy" insert ---;---.
        line 24; after "trifluoroalkyloxy insert ---;---.
        line 46; change "$r_1$" to ---$R_1$---.
        line 48; change "$r_1$" to ---$R_1$---.

Signed and Sealed this

Twelfth Day of January, 1993

*Attest:*

DOUGLAS B. COMER

*Attesting Officer*  *Acting Commissioner of Patents and Trademarks*